United States Patent
Kim et al.

(10) Patent No.: US 11,174,475 B2
(45) Date of Patent: *Nov. 16, 2021

(54) D-PSICOSE 3-EPIMERASE AND METHOD FOR PREPARING D-PSICOSE USING THE SAME

(71) Applicant: CJ CHEILJEDANG CORPORATION, Seoul (KR)

(72) Inventors: Su Jin Kim, Suwon-si (KR); Young Mi Lee, Suwon-si (KR); Yang Hee Kim, Suwon-si (KR); Seong Bo Kim, Seongnam-si (KR); Seung Won Park, Yongin-si (KR); Seong Jun Cho, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/461,286

(22) PCT Filed: Nov. 15, 2017

(86) PCT No.: PCT/KR2017/012970
§ 371 (c)(1),
(2) Date: May 15, 2019

(87) PCT Pub. No.: WO2018/093153
PCT Pub. Date: May 24, 2018

(65) Prior Publication Data
US 2020/0063117 A1    Feb. 27, 2020

(30) Foreign Application Priority Data
Nov. 16, 2016  (KR) ......................... 10-2016-0152947

(51) Int. Cl.
*C12P 19/02*    (2006.01)
*C12N 9/90*    (2006.01)
*C12N 1/20*    (2006.01)
*C12P 19/24*    (2006.01)

(52) U.S. Cl.
CPC .............. *C12N 9/90* (2013.01); *C12Y 501/03* (2013.01); *C12P 19/02* (2013.01); *C12P 19/24* (2013.01)

(58) Field of Classification Search
CPC ............ C12P 19/02; C12P 19/24; C12N 9/90; C12N 1/20; C12N 9/1051; C12N 15/70; C12N 9/1081; A23V 2250/606; C12Y 503/01006; C12Y 503/01005
See application file for complete search history.

(56) References Cited

U.S. PATENT DOCUMENTS 8,008,058 B2   8/2011   Kazuhiko et al.
9,217,166 B2   12/2015  Kim et al.

FOREIGN PATENT DOCUMENTS

| CN | 105637089 A | 6/2016 |
|---|---|---|
| EP | 2 990 483 A1 | 3/2016 |
| KR | 10-2014-0123284 A | 10/2014 |
| KR | 10-1539096 B1 | 7/2015 |
| KR | 10-2017-0075672 A | 7/2017 |
| WO | WO 2015/099256 A1 | 7/2015 |

OTHER PUBLICATIONS

Mu, et al., "Cloning, Expression, and Characterization of a D-Psicose 3-Epimerase from *Clostridium cellulolyticum* H10", J. Agric. Food Chem., Jun. 13, 2011, vol. 59, No. 14, pp. 7785-7792.
Zhang, et al., "Biochemical characterization of a D-psicose 3-epimerase from *Treponema primitia* ZAS-1 and its application on enzymatic production of D-psicose", J. Sci. Food Agric., Mar. 25, 2015, vol. 96, No. 1, pp. 49-56.
Zhang, et al., "Characterization of a Metal-Dependent D-Psicose 3-Epimerase from a Novel Strain, *Desmospora* sp. 8437", J. Agric. Food Chem., Nov. 7, 2013, vol. 61, No. 47, pp. 11468-11476.
Extended European Search Report and European Search Opinion dated May 19, 2020 in connection with related European Application No. EP 17 87 1550.
V Bilik, "Reactions of Saccharides Catalyzed by Molybdate ions. III. Preparation of L-Glucose by Epimerization of L-Mannose or L-Mannose Phenylhydrazone," Chem. Zvesti 28, pp. 187-189 (1972).
Landis W. Doner, "Isomerization of D-Fructose by Base: Liquid-Chromato-Graphic Evaluation and the Isolation of D-Pscicose", Carbohydrate Research, 70 (1979), pp. 209-216.
NCBI, GenBank Accession No. WP_018181373.1, Jul. 4, 2017.
International Search Report dated Feb. 14, 2018 in connection with PCT International Application No. PCT/KR2017/012970.
Written Opinion (form PCT/ISA/237) dated Feb. 14, 2018 in connection with PCT International Application No. PCT/KR2017/012970.
Office Action issued by the Russian Patent Office dated Feb. 27, 2020 in connection with Russian Patent Application No. 2019116720/10(031985), filed Nov. 15, 2017 to CJ Cheiljedang Corporation.

*Primary Examiner* — Tekchand Saidha
*Assistant Examiner* — Mohammad Y Meah
(74) *Attorney, Agent, or Firm* — John P. White

(57) ABSTRACT

Provided are a novel D-psicose 3-epimerase and a method for preparing psicose using the same.

3 Claims, 3 Drawing Sheets

Specification includes a Sequence Listing.

(a)

(b)

SEQUENCE LISTING

<160> NUMBER OF SEQ ID NOS: 5

<210> SEQ ID NO 1
<211> LENGTH: 297
<212> TYPE: PRT
<213> ORGANISM: Kaistia granuli

<400> SEQUENCE: 1

Met Lys Asn Lys Leu Gly Val His Ala Gln Val Trp Val Gly Gly Trp
1               5                   10                  15

Ser His Ala Glu Ala Glu Arg Ala Ile Ala Ser Thr Ala Ser Leu Gly
            20                  25                  30

Tyr Asp Tyr Ile Glu Ala Pro Ala Leu Asp Pro Ser Leu Ile Asp Ile
        35                  40                  45

Asp Phe Thr Arg Lys Ala Leu Glu Lys His Gly Leu Gly Ile Thr Thr
    50                  55                  60

Ser Leu Gly Leu Asp Asp Ser Cys Asp Ile Ser Ser Gly Asp Pro Asp
65                  70                  75                  80

Lys Lys Ala Arg Gly Gln Ala His Leu Met Lys Val Val Ser Thr Thr
                85                  90                  95

Arg Asp Leu Gly Gly Thr His Ile Thr Gly Ile Leu Tyr Ser Gly Phe
            100                 105                 110

Gln Lys Tyr Phe Thr Pro Ala Thr Pro Glu Gly Val Ala Gly Ala Val
        115                 120                 125

Glu Val Leu His His Val Ala Glu Gly Ala Ala Lys Ser Asn Ile Thr
    130                 135                 140

Leu Gly Leu Glu Val Val Asn Arg Tyr Glu Thr Asn Val Ile Asn Thr
145                 150                 155                 160

Ala Ala Gln Gly Val Glu Leu Cys Lys Arg Val Gly Met Pro Asn Val
                165                 170                 175

Lys Val His Leu Asp Cys Tyr His Met Asn Ile Glu Glu Ala Asp Ala
            180                 185                 190

Glu Arg Ala Ile Ile Asp Thr Gly Asp Tyr Leu Gly Tyr Phe His Thr
        195                 200                 205

Gly Glu Ser His Arg Gly Tyr Leu Gly Thr Gly Ser Ile Asp Phe Thr
    210                 215                 220

Arg Ile Phe Arg Gly Leu Val Lys Ala Asn Tyr Gln Gly Pro Ile Cys
225                 230                 235                 240

Phe Glu Ser Phe Ser Ser Ala Val Ala Gly Glu Pro Leu Ser Gly Ile
                245                 250                 255

Leu Gly Ile Trp Arg Asn Leu Trp Thr Asp Ser Thr Asp Leu Cys Arg
            260                 265                 270

His Ala Met Gln Phe Thr Gln Ala Gln Met Gln Ala Ala Glu Gln Ala
        275                 280                 285

Gln Ser Ile Arg Thr Gly Ala Asp Trp
    290                 295

<210> SEQ ID NO 2
<211> LENGTH: 894
<212> TYPE: DNA
<213> ORGANISM: Kaistia granuli

<400> SEQUENCE: 2
atgaagaaca agctgggtgt gcacgcacag gtctgggtcg gcggctggag ccatgcggag      60
gcggagcgcg ccatcgccag caccgcctcg ctcggctacg actatatcga ggcgccggcg     120

```
ctcgacccgt cgctgatcga catcgacttc acccgcaaag cgctggaaaa gcatggtctc      180
ggcatcacga cgtcgctcgg cctcgacgac agctgcgaca tctcctcggg cgatcccgac      240
aagaaggcgc gcggccaggc gcacctgatg aaggtggtct ccaccacccg tgatctcggc      300
ggcacccaca tcaccggtat cctctattcc ggcttccaga aatacttcac gcccgcaacg      360
ccggagggcg tcgccggcgc cgtcgaggta ttgcaccacg tcgccgagga agcggcgaag      420
agcaacatca cgctcggcct cgaggtggtg aaccgctacg agaccaacgt gatcaacacc      480
gccgcccagg gcgtcgagct ctgcaagcgg gtcggcatgc cgaacgtcaa ggtgcacctc      540
gactgctacc acatgaacat cgaggaagcc gacgccgagc gcgccatcat cgataccggc      600
gactatctgg gttatttcca taccggtgaa tcgcatcgcg gctatctcgg caccggctcg      660
atcgacttca cccgcatctt ccgcggcctg gtgaaggcca actaccaggg tccgatctgc      720
ttcgaatcct tctcgtccgc cgtcgccggc gagccgctct ccggcattct cggcatctgg      780
cgcaatctct ggacggattc gaccgatctc tgccgccacg ccatgcagtt cacgcaggca      840
cagatgcagg cggccgagca ggcccagtcg atccgcaccg cgcggactg gtag           894
```

<210> SEQ ID NO 3
<211> LENGTH: 22
<212> TYPE: DNA
<213> ORGANISM: Artificial Sequence
<220> FEATURE:
<223> OTHER INFORMATION: A forward primer of KGDPE

<400> SEQUENCE: 3

```
atgaagaaca agctgggtgt gc                                              22
```

<210> SEQ ID NO 4
<211> LENGTH: 20
<212> TYPE: DNA
<213> ORGANISM: Artificial Sequence
<220> FEATURE:
<223> OTHER INFORMATION: A reverse primer of KGDPE

<400> SEQUENCE: 4

```
tcaccagtcc gcgccggtgc                                                 20
```

<210> SEQ ID NO 5
<211> LENGTH: 289
<212> TYPE: PRT
<213> ORGANISM: Artificial Sequence
<220> FEATURE:
<223> OTHER INFORMATION: Amino acid sequence of ATPE

<400> SEQUENCE: 5

```
Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Leu Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95
```

```
Ala Lys Leu Asp Ile His Thr Ile Gly Gly Ala Leu His Ser Tyr Trp
            100             105             110

Pro Ile Asp Tyr Ser Gln Pro Val Asp Lys Ala Gly Asp Tyr Ala Arg
            115             120             125

Gly Val Glu Gly Ile Asn Gly Ile Ala Asp Phe Ala Asn Asp Leu Gly
            130             135             140

Ile Asn Leu Cys Ile Glu Val Leu Asn Arg Phe Glu Asn His Val Leu
145             150             155                         160

Asn Thr Ala Ala Glu Gly Val Ala Phe Val Lys Asp Val Gly Lys Asn
            165             170             175

Asn Val Lys Val Met Leu Asp Thr Phe His Met Asn Ile Glu Glu Asp
            180             185             190

Ser Phe Gly Asp Ala Ile Arg Thr Ala Gly Pro Leu Leu Gly His Phe
            195             200             205

His Thr Gly Glu Cys Asn Arg Arg Val Pro Gly Lys Gly Arg Met Pro
        210             215             220

Trp His Glu Ile Gly Leu Ala Leu Arg Asp Ile Asn Tyr Thr Gly Ala
225             230             235                         240

Val Ile Met Glu Pro Phe Val Lys Thr Gly Gly Thr Ile Gly Ser Asp
            245             250             255

Ile Lys Val Trp Arg Asp Leu Ser Gly Gly Ala Asp Ile Ala Lys Met
            260             265             270

Asp Glu Asp Ala Arg Asn Ala Leu Ala Phe Ser Arg Phe Val Leu Gly
            275             280             285

Gly
```

D-PSICOSE 3-EPIMERASE AND METHOD FOR PREPARING D-PSICOSE USING THE SAME

CROSS-REFERENCE TO RELATED APPLICATIONS

This application is a § 371 national stage of PCT International Application No. PCT/KR2017/012970, filed Nov. 15, 2017, claiming priority of Korean Patent Application No. KR 10-2016-'0152947, filed Nov. 16, 2016, the contents of each of which are hereby incorporated by reference into the application.

REFERENCE TO A SEQUENCE LISTING

This application incorporates-by-reference nucleotide and/or amino acid sequences which are present in the file named "200713 Substitute Sequence Listing AGD.txt", which is 7.00 kilobytes in size, and which was created Jul. 13, 2020 in the IBM-PC machine format, having an operating system compatibility with MS-Windows, which is contained in the text file which is being submitted as part of this application.

TECHNICAL FIELD

The following disclosure relates to a D-psicose 3-epimerase and a method for preparing D-psicose using the same.

BACKGROUND

D-psicose (hereinafter referred to as "psicose") is a monosaccharide known as a rare sugar present in a very small amount in the natural world. It has almost zero calorie while having nearly 70% sweetness of sugar and has received a lot of attention as a new food ingredient due to its functionalities such as inhibition of blood glucose, and inhibition of lipid synthesis, etc.

Due to these characteristics, psicose is considered to be used as a sweetener substitute for sugar in various foods. However, there is an increasing need for a method for efficiently preparing psicose since it exists in a very small amount in the natural world.

A known method for preparing psicose includes a method for utilizing catalysis of molybdate ions (Bilik, V., Tihlarik, K., 1973, Reaction of Saccharides Catalyzed by Molybdate Ions. IX. Epimerization of Ketohexoses. Chem. Zvesti. 28:106-109), A Chemical Method for Preparing Psicose from D-Fructose by Heating Ethanol and Triethylamine Together (Doner, L. W., 1979, Isomerization of D-Fructose by Base: Liquid-Chromatographic Evaluation and The Isolation of D-Psicose. Carbohydr. Res. 70:209-216), and A Biological Method for Preparing Psicose from D-Fructose Using a Microorganism that Produces D-Psicose 3-Epimerase (Korean Patent Laid-Open Publication No. 10-2011-0035805). Preparation of psicose by the chemical method has problems in that a large amount of byproducts occur, and thus, it is required to perform a complicated purification. Further, the biological method also has problems in that the yield is very low and the preparation cost is high.

Under these circumstances, the present inventors have made a lot of effort to develop a method for improving a preparation yield of the psicose, and as a result, confirmed that when the novel D-psicose-3-epimerase (hereinafter referred to as "psicose epimerase") of the present invention was used, a rate at which D-fructose is converted to psicose (hereinafter, referred to as a conversion rate from D-fructose to psicose) was increased to thereby be able to remarkably increase the preparation yield of the psicose, and completed the present invention.

Technical Problem

An embodiment of the present invention is directed to providing a novel psicose epimerase, a polynucleotide encoding the psicose epimerase, a recombinant vector including the polynucleotide, and a microorganism into which the vector is introduced.

Another embodiment of the present invention is directed to providing a composition for preparing D-psicose including a psicose epimerase, a microorganism expressing the psicose epimerase, or a culture of the microorganism, and a method for preparing D-psicose using the psicose epimerase.

Technical Solution

According to an exemplary embodiment of the present invention, there is provided a D-psicose 3-epimerase consisting of amino acid sequence of SEQ ID NO: 1.

In an exemplary embodiment, the psicose epimerase may include a polypeptide having at least 80%, 90%, 95%, 97% or 99% homology with the amino acid sequence of SEQ ID NO: 1. It is obvious that the amino acid sequence having an activity of converting D-fructose to psicose and the above-described homology may include a case where a part of the amino acid sequence of SEQ ID NO: 1 is substituted, inserted, modified and/or deleted. In addition, polypeptides having a psicose epimerase activity may also be included without limitation as a polypeptide encoded by a polynucleotide that is hybridized with a complementary sequence to all or a part of the nucleotide sequence encoding a probe that is able to be prepared from a known gene sequence, for example, the psicose epimerase of the present invention, under stringent condition.

The term "polynucleotide" as used herein refers to polyribonucleotide or polydeoxyribonucleotide in which a nucleotide monomer is unmodified or modified to a polymer of nucleotides extended in a long chain by covalent bonds.

The term "stringent condition" as used herein means a condition that allows specific hybridization between polynucleotides. The condition depends on a length of the polynucleotide and a degree of complementarity. Parameters thereof are well known in the art and are specifically described in the document (e.g., J. Sambrook et al., supra). For example, the stringent condition may list a condition for hybridizing genes to each other each having high homology of 80%, 90%, 95%, 97%, or 99% or more, a condition for not hybridizing genes to each other each having homology lower than that, or a general washing condition of southern hybridization, i.e., a condition for washing once, specifically two to three times at a salt concentration and a temperature such as 60° C., 1×SSC, 0.1% SDS, specifically, 0° C., 0.1×SSC, 0.1% SDS, and more specifically, 68° C., 0.1× SSC, 0.1% SDS. The probe used in the hybridization may be a part of the complementary sequence of the base sequence. Such a probe may be constructed by a PCR using a gene fragment including the base sequence as a template, by utilizing an oligonucleotide prepared based on the known sequence as a primer. Further, those skilled in the art may adjust the temperature and the salt concentration of the wash solution as needed depending on factors such as a length of the probe.

The term "homology" as used herein refers to a percentage of identity between two polynucleotides or polypeptide moieties. The homology between sequences from one moiety to another moiety may be determined by known techniques. For example, the homology may be determined by directly aligning parameters of sequence information between two polynucleotide molecules or two polypeptide molecules, such as score, identity, and similarity, etc., using a computer program that sorts sequence information and is readily available (e.g., BLAST 2.0). Further, the homology between polynucleotides may be determined by hybridization of the polynucleotide under a condition in which a stable double strand is formed between homologous regions, followed by degradation by a single-strand-specific nuclease to determine a size of the degraded fragment.

Further, as long as a protein has an activity corresponding to a psicose epimerase consisting of the amino acid sequence of SEQ ID NO: 1 of the present invention, it is possible to add a nonsense sequence before and after the amino acid sequence of SEQ ID NO: 1, or to include a naturally occurring mutation or a silent mutation thereof. The protein including the amino acid sequence of SEQ ID NO: 1 is also included within the scope of the present invention.

In addition, the D-psicose-3-epimerase of the present invention may be encoded by a polynucleotide sequence of SEQ ID NO: 2, or a polynucleotide sequence having at least 80%, 90%, 95%, 97% or 99% homology thereto, but the present invention is not limited thereto. Further, it is obvious that as to the polynucleotide encoding the D-psicose-3-epimerase of the present invention, a polynucleotide capable of being translated into a protein consisting of the amino acid sequence of SEQ ID NO: 1 or a protein having homology thereto by codon degeneracy may also be included within the polynucleotide sequence range of the present invention. Those skilled in the art will understand that it is possible to prepare a polynucleotide encoding an enzyme having a substantially equivalent activity range by substituting, adding, and/or deleting one or more of the nucleotide sequence of SEQ ID NO: 2 using known recombinant techniques.

In another exemplary embodiment, the psicose epimerase of the present invention may be derived from a microorganism of the genus *Kaistia*. Specifically, the psicose epimerase of the present invention may be derived from *Kaistia granuli*, and more specifically, may be derived from *Kaistia granuli* KCTC 12575.

In another exemplary embodiment, the psicose epimerase of the present invention may have a molecular weight of 25 kDa to 37 kDa, 27 kDa to 35 kDa, or 30 kDa to kDa, as measured via sodium dodecyl sulfate polyacrylamide gel electrophoresis (SDS-PAGE).

According to another exemplary embodiment of the present invention, there is provided a polynucleotide encoding the D-psicose 3-epimerase consisting of amino acid sequence of SEQ ID NO: 1.

In an exemplary embodiment, the polynucleotide provided herein may be a polynucleotide consisting of base sequence of SEQ ID NO: 2 or a sequence having 80%, 90%, 95%, 97%, or 99% or more homology with the base sequence of SEQ ID NO: 2. Further, it is obvious that as to the polynucleotide provided herein, a polynucleotide capable of being translated into a protein consisting of the amino acid sequence of SEQ ID NO: 1 or a protein having homology thereto by codon degeneracy is also included within the range of the present invention.

According to another exemplary embodiment of the present invention, there is provided a recombinant vector including a polynucleotide encoding the D-psicose 3-epimerase of the present invention.

The recombinant vector of the present invention may have a form in which the polynucleotide encoding the psicose epimerase is inserted into a cloning vector or an expression vector using known standard methods. The term "cloning vector" as used herein refers to a vector capable of carrying a DNA fragment into a host cell and regenerating it. The cloning vector may further include a polyadenylation signal, a transcription termination sequence, and/or a multiple cloning site. Here, the multiple cloning site may include at least one of an endonuclease and a restriction enzyme site. In an exemplary embodiment, the polynucleotide encoding the psicose epimerase may be located upstream of the polyadenylation signal and the transcription termination sequence. The term "expression vector" as used herein refers to the DNA sequence necessary for transcription and translation of the cloned DNA in an appropriate host. Further, "expression vector" as used herein refers to a gene construct including an essential regulatory element operably linked to an insert such that the insert is expressed when present in a cell of a subject. The term "operably linked" means that one function is regulated by another one by polynucleotide sequence association on a polynucleotide. The expression vector may be prepared and purified using standard recombinant DNA techniques. The expression vector may include at least any one of a promoter, an initiation codon, a gene encoding a cytosine epimerase, and a termination codon.

According to another exemplary embodiment of the present invention, there is provided a microorganism into which the recombinant vector as described above is introduced.

In an exemplary embodiment, the microorganism into which the recombinant vector of the present invention is introduced may be a microorganism which is transformed with the recombinant vector including the polynucleotide encoding a psicose epimerase including the amino acid sequence of SEQ ID NO: 1, or by the recombinant vector including the polynucleotide consisting of the base sequence of SEQ ID NO: 2.

The term "transformation" as used herein means that a gene or a recombinant vector including the gene is introduced into a host cell so that the gene is able to be expressed in the host cell. The present invention includes any transformed gene as long as the transformed gene is able to be expressed in the host cell, without limitation, whether it is inserted into a chromosome of the host cell or is located outside the chromosome of the host cell. The transformation method of the present invention includes transient transformation, microinjection, transduction, cell fusion, calcium phosphate precipitation, liposome-mediated transfection, DEAE dextran mediated transfection, electric perforation, electric injection, chemical treatment, etc., but the present invention is not limited thereto. A host cell capable of being transformed with the recombinant vector may include a prokaryotic cell, a plant cell, an animal cell, etc. A host cell having high DNA introduction efficiency and high expression rate of introduced DNA may be used. For example, the host cell may be *E. coli*, a strain of the genus *Bacillus*, a strain of the genus *Corynebacterium*, a strain of the genus *Salmonella*, etc., and for example, may be *E. coli* such as W3110, BL21, JM109, K-12, LE392, RR1 and DH5a, etc.

More specifically, the microorganism of the present invention may be *E. coli* BL21(DE3)/KGDPE deposited with KCCM11918P.

According to another exemplary embodiment of the present invention, there is provided a composition for preparing D-psicose including: the D-psicose 3-epimerase including amino sequence of SEQ ID NO: 1, a microorganism expressing the D-psicose 3-epimerase, a culture of the microorganism.

In an exemplary embodiment, the microorganism of the present invention may be a strain itself, a culture thereof, or a disruption of the microorganism. The culture or disruption of the present invention may include the D-psicose-3-epimerase of the present invention. In addition, the culture of the microorganism of the present invention may or may not include the microorganism. Further, the disruption of the microorganism of the present invention may be a disruption obtained by disrupting a microorganism or a culture thereof, or a supernatant obtained by centrifuging the disruption.

In another exemplary embodiment, the composition for preparing the D-psicose of the present invention may further include D-fructose as a substrate of the psicose epimerase.

In another exemplary embodiment, the microorganism of the present invention may be immobilized on a carrier to be used. An example of the carrier that is able to be used in the present invention includes, but is not limited to, agar, agarose, k-carrageenan, alginate or chitosan.

Further, the composition for preparing the D-psicose of the present invention may further include any component capable of supporting the preparation of the psicose. Specifically, the composition for preparing the D-psicose of the present invention may further include a metal. More specifically, the metal of the present invention may be at least one metal selected from the group consisting of manganese, calcium, magnesium, iron, lithium and sodium. In addition, the metal of the present invention may be a metal ion or a metal salt. The metal of the present invention may have a concentration of 0.1 mM to 10 mM, 0.1 mM to 7 mM, 0.1 mM to 4 mM, 0.5 mM to 10 mM, 0.5 mM to 7 mM, 0.5 mM to 4 mM, 1 mM to 10 mM, 1 mM to 7 mM, 1 mM to 4 mM, 2 mM to 10 mM, 2 mM to 7 mM, or 2 mM to 4 mM. More specifically, the metal salt of the present invention may be at least one metal salt selected from the group consisting of LiCl, $Na_2SO_4$, $MgCl_2$, NaCl, $FeSO_4$, $MgSO_4$, $MnCl_2$, $MnSO_4$, and $CaCl_2$.

According to another exemplary embodiment of the present invention, there is provided a method for preparing D-psicose, including: contacting the D-psicose 3-epimerase consisting of amino acid sequence of SEQ ID NO: 1, a microorganism expressing the D-psicose 3-epimerase, or a culture of the microorganism with D-fructose.

In an exemplary embodiment, the preparation method may further include, before, after or simultaneously with the contacting with the D-fructose, adding a metal.

In another exemplary embodiment, the preparation method may further include, after the contacting with the D-fructose or the adding of the metal, isolating and/or purifying a contact result including the psicose. The isolating and/or purifying may be performed by one or more known methods such as dialysis, precipitation, adsorption, electrophoresis, ion exchange chromatography and fractional crystallization, etc., but is not limited thereto.

Further, the preparation method of the present invention may further include, before or after the isolating and/or purifying, performing decoloration and/or desalination. By performing the decolorization and/or desalination, it is possible to obtain more refined psicose without impurities.

In another exemplary embodiment, the preparation method of the present invention may further include, after the contacting with the D-fructose, the adding of the metal, the isolating and/or purifying, or the performing of the decoloration and/or the desalination, crystallizing the D-psicose. The crystallization may be performed by using a crystallization method which is conventionally used. For example, the crystallization may be performed by using a cooling crystallization method.

In another exemplary embodiment, the preparation method of the present invention may further include, before the crystallizing, concentrating the psicose. The concentration may increase a crystallization efficiency.

In another embodiment, the preparation method of the present invention may further include, after the isolating and/or purifying, contacting an unreacted D-fructose with the psicose epimerase, or may further include, after the crystallizing, re-using a mother liquor from which crystallization is isolated in the isolating and/or purifying, or a combination thereof. Through the additional steps, the psicose may be obtained in a higher yield and an amount of D-fructose to be discarded may be reduced, thereby providing economic benefits.

In an exemplary embodiment, the contacting of the present invention may be performed at pH 5.0 to 9.0, at 40 to 90° C., and/or for 0.5 to 48 hours.

Specifically, the contacting of the present invention may be performed at pH of 6.0 to 8.5, at pH of 6.0 to 8.0, or at pH of 7.0 to 8.0.

In addition, the contacting of the present invention may be performed at a temperature of 40° C. to 80° C., 40° C. to 75° C., 40° C. to 65° C., 50° C. to 90° C., 50° C. to 80° C., 50° C. to 75° C., 50° C. to 65° C., 55° C. to 90° C., 55° C. to 80° C., 55° C. to 75° C., 55° C. to 65° C., 60° C. to 90° C., 60° C. to 80° C., 60° C. to 75° C., 60° C. to 65° C., 65° C. to 90° C., 65° C. to 80° C. or 65° C. to 75° C.

In addition, the contacting of the present invention may be performed for 0.5 hour or more, 1 hour or more, 3 hours or more, 5 hours or more, or 6 hours or more, and/or 48 hours or less, 36 hours or less, 24 hours or less, 12 hours or less, 9 hours or less.

The psicose epimerase, metal and carrier described in the method for preparing D-psicose of the present invention are the same as described in the above-described exemplary embodiments.

According to still another exemplary embodiment of the present invention, there is provided use of the psicose epimerase, the microorganism expressing the psicose epimerase, or the culture of the microorganism as described herein for conversion of D-fructose in the preparation of the psicose.

Effect of Invention

The psicose epimerase of the present invention is excellent in an activity of converting D-fructose to psicose, has high-temperature stability to the extent that it is industrially available, and has a rapid conversion reaction rate. Accordingly, when the psicose epimerase of the present invention is used to prepare the psicose, it is possible to prepare the psicose with high efficiency and high yield.

BRIEF DESCRIPTION OF THE DRAWINGS

FIGS. 3A and 3B are graphs showing a relative enzymatic activity of the psicose epimerase according to temperature, wherein FIG. 3A shows an activity of a D-psicose 3-epimerase (ATPE) derived from Agrobacterium tumefaciens in the prior art, and FIG. 3B shows an activity of KGDPE in the present invention.

DETAILED DESCRIPTION OF EMBODIMENTS

Hereinafter, the present invention will be described in more detail by the following Examples. However, the present invention is not limited to the Examples below, and it should be understood that various modifications and changes may be made by those skilled in the art within the scope and spirit of the present invention.

Throughout the specification of the present invention, unless otherwise noted, "%" used to denote a concentration of a specific material refers to a solid/solid (weight/weight) %, a solid/liquid (weight/volume) %, and a liquid/liquid (volume/volume) %.

EXAMPLES

Example 1. Preparation of Transformed Strain that Prepares Psicose Epimerase Derived from Microorganism of Genus Kaistia A gene which was expected to have activity of a psicose epimerase that converts D-fructose to psicose from the microorganism of the genus *Kaistia* was selected, and a recombinant expression vector including the gene and a transformed microorganism were prepared.

Figure 1:
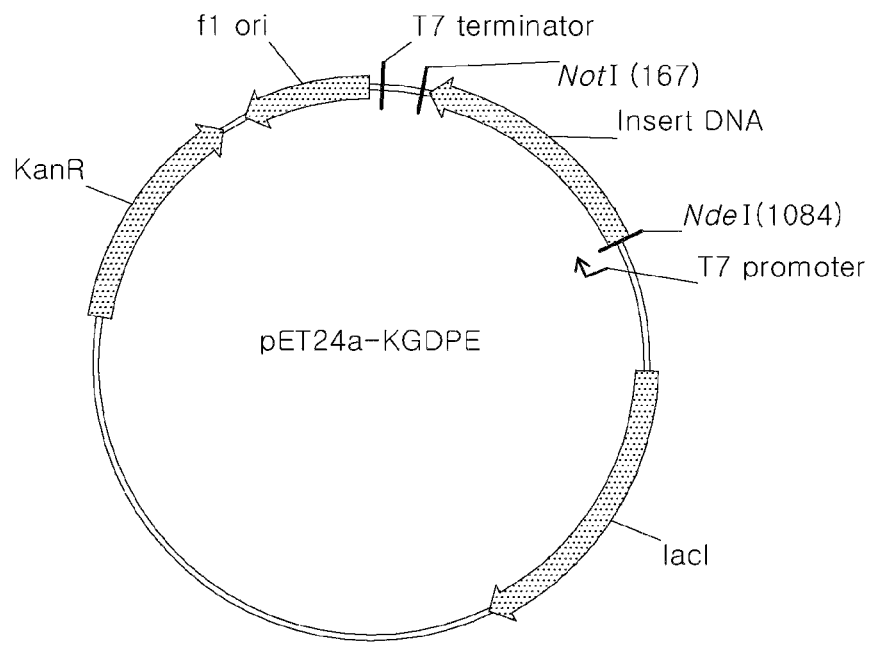
FIG. 1 is a diagram of a recombinant vector for expressing a psicose epimerase (KGDPE) consisting of amino acid sequence of SEQ ID NO: 1 of the present invention.

Specifically, a gene kgdpe of *Kaistia granuli* KCTC 12575, which was expected to be a psicose epimerase, was selected from the gene sequences of the microorganism of the genus *Kaistia* registered at Genbank, and a forward primer (SEQ ID NO: 3) and a reverse primer (SEQ ID NO: 4) were designed and synthesized based on the amino acid sequence (SEQ ID NO: 1) and the nucleotide sequence (SEQ ID NO: 2) of the gene. By using the synthesized primer, a gene was amplified by performing a PCR reaction (33 cycles: 1 cycle including 94° C. for 1 minute, 58° C. for 30 seconds, and 72° C. for 1 minute) using a genomic DNA of *Kaistia granuli* KCTC 12575 as a template. The amplified gene was purified using a PCR purification kit (Quiagen) and inserted into pET24a(+) (novagen, USA) using restriction enzymes NdeI and notI to construct a recombinant vector pET24a(+)-KGDPE (FIG. 1).

The recombinant vector was transformed into *Escherichia coli* BL21 (DE3) by heat shock transformation (Sambrook and Russell: Molecular Cloning, 2001), and then stored frozen in 50% glycerol and used. The transformed strain was named *E. coli* BL21(DE3)/KGDPE, deposited on Oct. 20, 2016 in the Korean Culture Center of Microorganisms (KCCM) which is an international depository under the Budapest Treaty, and granted accession number KCCM11918P.

Example 2. Preparation and Purification of Psicose Epimerase

To prepare the psicose epimerase from *E. coli* BL21 (DE3)/KGDPE prepared in Example 1, *E. coli* BL21(DE3)/KGDPE was inoculated into 5 ml of LB-kanamycin medium, and was subjected to shake-culture at 37° C., 200 rpm until the absorbance measured at 600 nm reached 1.5. Then, the shake-cultured culture liquid was inoculated into 500 ml of LB-kanamycin medium, and when the absorbance at 600 nm was 0.7, 0.5 mM of isopropyl β-D-1-thiogalactopyranoside (IPTG) was added, and the cells were main-cultured at 16° C. and 150 rpm for 16 hours.

The main-cultured culture liquid was centrifuged at 8000 rpm for 20 minutes to recover only the cells, and the cells were washed twice with 0.85% (w/v) NaCl and then lysed in a lysis buffer (50 mM Tris-HCl, pH 7.0 300 mM NaCl), and disrupted at 4° C. for 20 minutes using a sonic vibrator. The disrupted liquid was centrifuged at 4° C., 13,000 rpm for 20 minutes to recover the supernatant. Then, the supernatant was applied to a Ni-NTA column (Ni-NTA Superflow, Qiagen) previously equilibrated with the above lysis buffer, and a buffer solution (50 mM Tris-HCl, 300 mM NaCl, pH 7.0) containing 250 mM imidazole was sequentially flowed to obtain a purified psicose epimerase (hereinafter, referred to as KGDPE). The SDS-PAGE of the KGDPE confirmed that the size of the monomer was about 32 kDa.

Example 3. Confirmation of KGDPE Activity 3-1. Confirmation of Conversion Activity from D-fructose to Psicose To confirm whether the KGDPE prepares psicose using D-fructose as a substrate, KGDPE (50 mM Tris-HCl, pH 7.0) prepared in Example 2 was added to 50 mM Tris-HCl buffer (pH 8.0) containing 50 wt % D-fructose and 3 mM $MnSO_4$, and reacted at 55° C. for 6 hours. Then, the reaction was stopped by heating at 100° C. for 5 minutes, and then the preparation of the psicose was confirmed by HPLC analysis. The HPLC analysis was performed using HPLC (Agilent, USA) Refractive Index Detector (Agilent 1260 RID) equipped with Aminex HPX-87C column (BIO-RAD), wherein a mobile phase solvent was water, a temperature was 80° C., and a flow rate was 0.6 ml/min.

Figure 2:
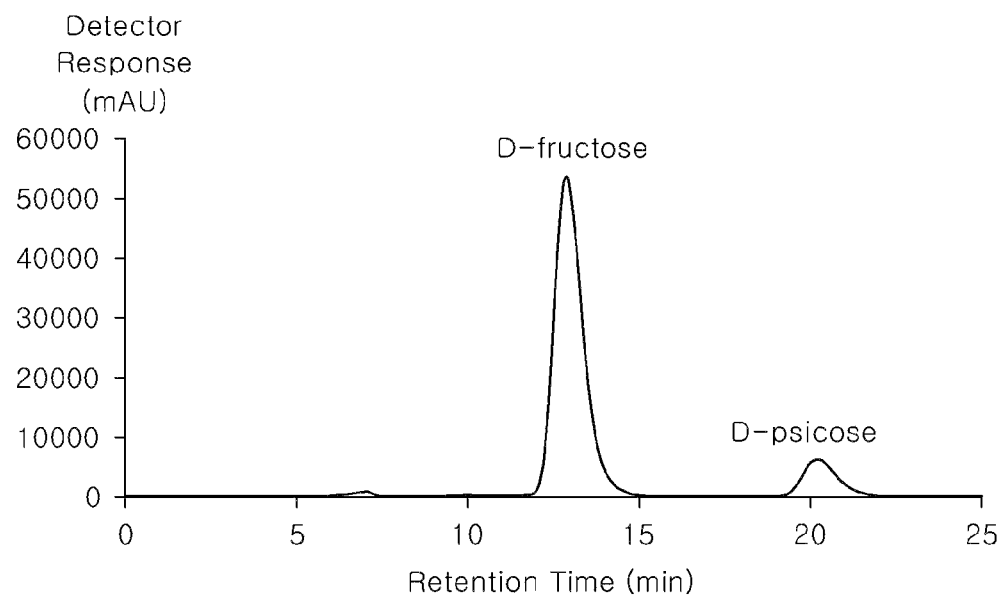
FIG. 2 is HPLC analysis data on results of psicose preparation utilizing D-fructose as a substrate using the KGDPE of the present invention.

As a result, it was confirmed that the psicose could be prepared from the D-fructose using KGDPE (FIG. 2).

3-2. Confirmation of Conversion Activity from D-fructose to Psicose

To confirm whether the preparation ability of the KGDPE is superior to that of the conventional psicose epimerase (ATPE, SEQ ID NO: 5, Korean Patent Laid-Open Publication No. 10-2011-0035805) used in the preparation of the psicose, a conversion rate from the D-fructose to the psicose was confirmed.

Specifically, *E. coli* BL21 (DE3) transformed with the recombinant expression vector pET24a-ATPE was inoculated into LB medium containing kanamycin having a concentration of 10 μg/ml, and then the enzyme was expressed and purified in the same manner as in Example 2. The obtained enzyme was added to 50 mM Tris-HCl buffer (pH 8.0) containing 50 wt % D-fructose and 3 mM $MnSO_4$ and reacted at 55° C. for 6 hours. Then, the reaction was stopped by heating at 100° C. for 5 minutes, and then the preparation of the psicose was confirmed by HPLC analysis. The HPLC analysis was performed under the same conditions as in Example 3-1. The conversion rate to psicose was calculated as the amount (mg/min) of the psicose prepared per minute by the enzyme, and the reaction rate of KGDPE was shown as a relative value, wherein the reaction rate value of ATPE was set to 100%.

As a result, it was confirmed that the amount of the psicose prepared per minute when using the KGDPE was 117.6% as compared to when using the ATPE, and thus, the conversion rate from D-fructose to psicose was remarkably increased when the KGDPE was used (Table 1).

TABLE 1

| Enzyme | KGDPE | ATPE |
|---|---|---|
| Relative conversion rate (%) | 117.6 | 100 |

Example 4. Analysis of KGDPE Characteristics

4-1. Analysis of Enzyme Activity According to Temperature

The KGDPE and the D-fructose substrate were reacted for 2 hours under various temperature conditions (40° C., 45° C., 50° C., 55° C., 60° C., 65° C., 70° C. and 75° C.), and enzyme activities according to the temperatures were compared. The above reactions were performed in the same manner as in Example 3-1 except for the temperature and the reaction time, and the enzyme activities were measured as the conversion rate from the D-fructose to the psicose. The conversion rate was calculated as the percentage of weight of the psicose prepared after the reaction relative to a weight of the substrate (D-fructose) before the reaction.

As a result, the KGDPE exhibited a high conversion activity of 25% or more at all measurement temperature ranges, and it was confirmed that as the temperature increased, the activity increased and the maximum conversion rate was observed at the maximum temperature of 75° C. (Table 2).

TABLE 2

| Temperature (° C.) | KGDPE (Conversion rate, %) |
|---|---|
| 40 | 26.7 |
| 45 | 27.8 |
| 50 | 28.8 |
| 55 | 29.7 |
| 60 | 30.5 |
| 65 | 31.2 |
| 70 | 32.1 |
| 75 | 32.8 |

4-2. Analysis of Thermal Stability of Enzyme

To compare thermal stability of the KGDPE with that of the conventional enzyme ATPE, the respective enzymes were heat-treated at various temperatures (55° C., 60° C. and 65° C.), and enzymatic treatment solutions were sampled for each heat treatment time (0.5 hour, 1 hour, 2 hours, 3 hours, 4 hours, 5 hours and 6 hours) to determine residual activity of each enzyme. The reaction was performed for 30 minutes by changing the reaction time only in the same manner as in Example 3-1, and the residual activity of the enzyme was measured by the conversion rate from the D-fructose to the psicose.

Figure 3:
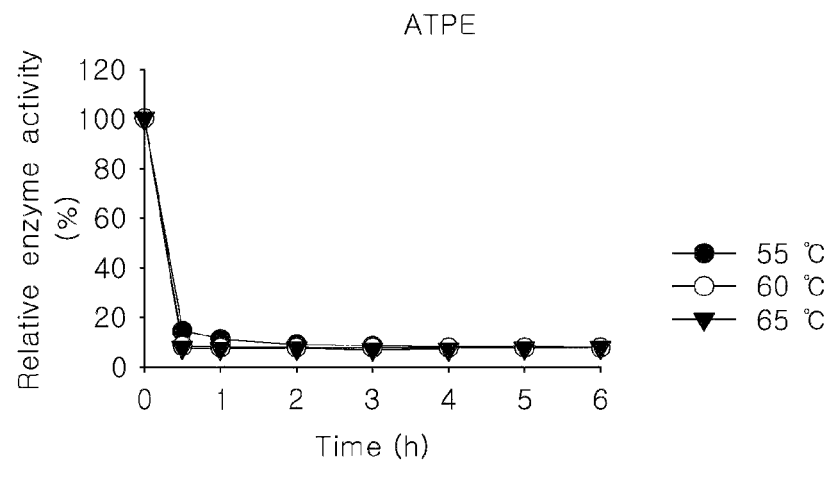
Figure 3:
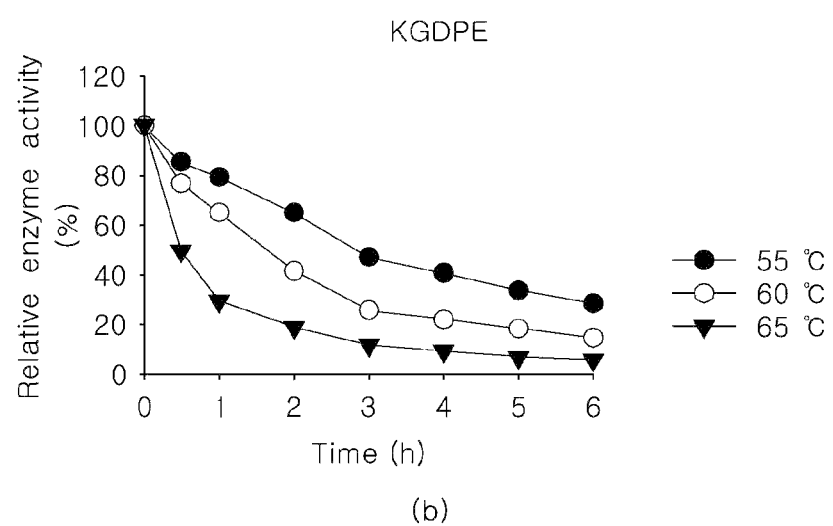

As a result, the reduction of the half life of the KGDPE according to the temperature increase was remarkably smaller than that of the ATPE, and thus, it was confirmed that the KGDPE had high thermal stability (FIGS. 3A and 3B).

4-3. Analysis of Enzyme Activity According to pH

To determine the enzyme activity according to pH, the D-fructose substrate was reacted with KGDPE at various pHs. At this time, the reaction was performed in the same manner as in Example 3-1 except for the reaction time and pH.

Specifically, the enzyme reaction was performed at 55° C. for 30 minutes by using 50 mM potassium phosphate at pH 5.0, pH 6.0, pH 6.5, pH 7.0, pH 7.5, and pH 8.0, and using a 50 mM Tris-HCl buffer at pH 8.0, pH 8.5, and pH 9.0. Then, the enzyme activity was measured as the conversion rate from the D-fructose to the psicose.

Figure 4:
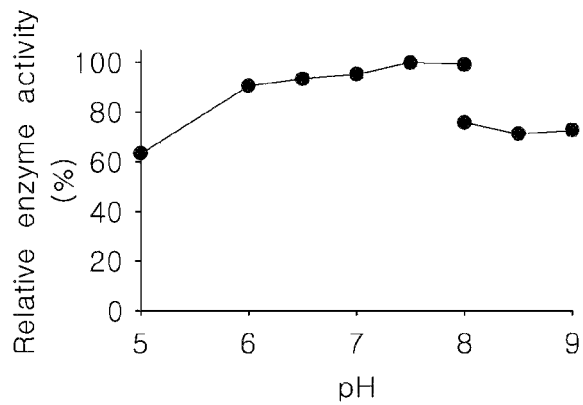
FIG. 4 is a graph showing relative enzymatic activity of the KGDPE of the present invention according to pH change.

As a result, it was confirmed that the KGDPE exhibited activity of 70% or more as compared to the maximum activity at pH 6 to pH 8.5, and exhibited the highest activity at pH 8.0 (Table 3, FIG. 4).

TABLE 3

| pH | | Relative conversion rate (%) |
|---|---|---|
| 50 mM potassium phosphate | 5 | 63 |
| | 6 | 91 |
| | 6.5 | 93 |
| | 7 | 95 |
| | 7.5 | 100 |
| | 8 | 99 |
| 50 mM Tris-HCl | 8 | 76 |
| | 8.5 | 71 |
| | 9 | 73 |

4-4. Activity Analysis of Enzyme According to Addition of Metal

To confirm the activity of the KGDPE according to a metal addition, under the same reaction conditions as in Example 3-1, $MnSO_4$ was replaced with various metal salts (LiCl, $Na_2SO_4$, $MgCl_2$, NaCl, $FeSO_4$ and $CaCl_2$) and added to a final concentration of 3 mM. Then, the enzyme activity was measured. The control group was not treated with the metal salts.

Figure 5:
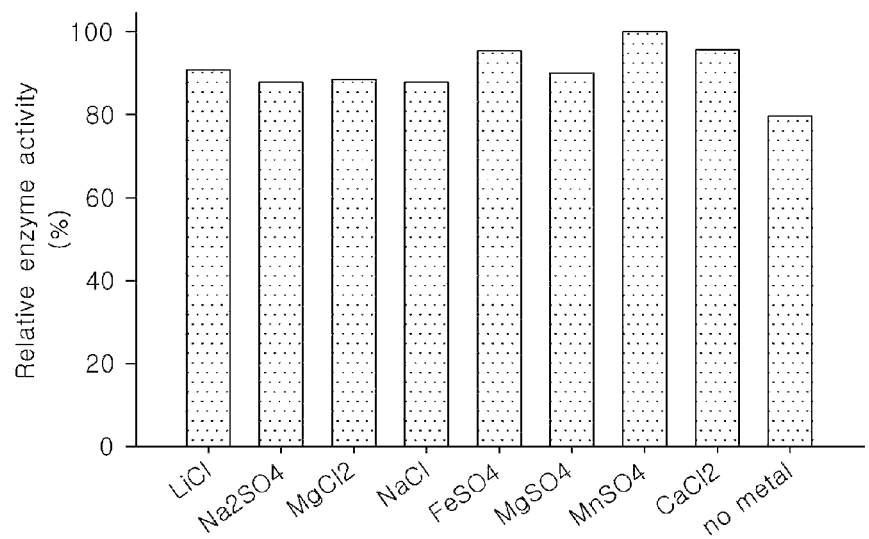
FIG. 5 is a graph showing relative enzymatic activity of the KGDPE of the present invention according to addition of various metals.

As a result, it was confirmed that the addition of Li, Na, Mg, Fe and Ca as well as Mn increased the activity of the KGDPE as compared to the control group, and among them, it could be confirmed that Mn increased the enzyme activity the most (Table 4 and FIG. 5).

TABLE 4

| Metal Salt | Relative enzyme activity (%) |
|---|---|
| LiCl | 91 |
| $Na_2SO_4$ | 88 |
| $MgCl_2$ | 88 |
| NaCl | 88 |
| $FeSO_4$ | 95 |
| $MgSO_4$ | 90 |
| $MnSO_4$ | 100 |
| $CaCl_2$ | 96 |
| no metal | 79 |

From the above description, it will be understood by those skilled in the art that the present invention can be made in other specific forms without modifying a technical idea or essential characteristics thereof. In this regard, it should be understood that the embodiments described above are illustrative in all aspects and not restrictive. The scope of the present invention should be interpreted to cover all modifications or variations derived from the meaning and scope of the appended claims and their equivalents rather than the detailed description.

What is claimed is:

1. A method for preparing D-psicose, comprising: contacting a D-psicose 3-epimerase consisting of the amino acid sequence of SEQ ID NO: 1, a microorganism expressing the D-psicose 3-epimerase, or a culture of the microorganism with D-fructose.

2. The method of claim 1, wherein the contacting is performed at pH of 5.0 to 9.0, at a temperature of 40° C. to 90° C., or for 0.5 to 48 hours.

3. The method of claim 1, further comprising: before, after or simultaneously with the contacting of the D-fructose, contacting the D-psicose 3-epimerase, the microorganism expressing the D-psicose 3-epimerase, or the culture of the microorganism with a metal.

* * * * *